(12) United States Patent
Yang

(10) Patent No.: US 7,048,922 B2
(45) Date of Patent: May 23, 2006

(54) STIMULATION OF HEMATOPOIESIS BY EX VIVO ACTIVATED IMMUNE CELLS

(76) Inventor: Demao Yang, 1921 Rock St., Suite 16, Mountain View, CA (US) 94043

(*) Notice: Subject to any disclaimer, the term of this patent is extended or adjusted under 35 U.S.C. 154(b) by 199 days.

(21) Appl. No.: 10/159,148

(22) Filed: May 29, 2002

(65) Prior Publication Data

US 2003/0223968 A1    Dec. 4, 2003

(51) Int. Cl.
*A61K 35/14* (2006.01)
*C07K 14/475* (2006.01)
*C07K 14/55* (2006.01)

(52) U.S. Cl. .................... 424/93.7; 514/12; 530/351; 530/399

(58) Field of Classification Search ............... 424/93.1, 424/93.7; 514/2, 12; 435/4, 325, 375, 377, 435/383, 395
See application file for complete search history.

(56) References Cited

U.S. PATENT DOCUMENTS

| | | | |
|---|---|---|---|
| 5,015,664 A | 5/1991 | Green | |
| 5,047,421 A | 9/1991 | Green | |
| 5,108,760 A | 4/1992 | Irr et al. | |
| 5,506,267 A | 4/1996 | Aono et al. | |
| 5,525,232 A | 6/1996 | Veiro et al. | |
| 5,550,161 A | 8/1996 | Green | |
| 5,616,612 A | 4/1997 | Ayral-Kaloustian et al. | |
| 5,643,786 A | 7/1997 | Cohen et al. | |
| 5,658,945 A | 8/1997 | Ayral-Kaloustian et al. | |
| 5,766,920 A | 6/1998 | Babbitt et al. | |
| 5,932,446 A | 8/1999 | Gallagher et al. | |
| 5,968,513 A | 10/1999 | Gallo et al. | |
| 5,994,126 A | 11/1999 | Steinman et al. | |
| 6,008,042 A | 12/1999 | Dixit et al. | |
| 6,010,878 A | 1/2000 | Dixit et al. | |
| 6,010,905 A | 1/2000 | Cohen et al. | |
| 6,033,661 A | 3/2000 | Smith et al. | |
| 6,187,821 B1 | 2/2001 | Fujita et al. | |
| 6,203,787 B1 | 3/2001 | Thompson et al. | |
| 6,294,169 B1 | 9/2001 | Dixit et al. | |
| 6,340,461 B1 | 1/2002 | Terman | |
| 6,352,694 B1 | 3/2002 | June et al. | |
| 2001/0027215 A1 | 10/2001 | Perrine | |

FOREIGN PATENT DOCUMENTS

| | | | |
|---|---|---|---|
| EP | 1 077 254 A2 | | 2/2001 |
| WO | WO 95/20649 A1 | | 8/1995 |
| WO | WO 96/23060 | * | 8/1996 |
| WO | WO 98/06823 A2 | | 2/1998 |
| WO | WO 01/34788 A1 | | 5/2001 |
| WO | WO 01/62092 A1 | | 8/2001 |
| WO | WO 02/36748 A2 | | 5/2002 |

OTHER PUBLICATIONS

Brugger et al. Ex vivo expansion of enriched peripheral blood CD34+ progenitor cells by stem cell factor, interleukin-1beta, IL-6, IL-3, interferon-gamma, and erythropoietin. Blood 81: 2579-2584, 1993.*
Waclavicek et al. Calcium ionophore: a single reagent for the differentiation of primary human acute myelogenous leukaemia cells towards dendritic cells. Brit J Haematol 114(2): 466-473, 2001.*
Chen et al. Ex vivo immunotherapy for patients with benzene-induced aplastic anemia. J Hematotherapy and stem cell research 12(5): 505-514, 2003.*
Shah et al. Why do we still use serum in the production of biopharmaceuticals? Dev Biol Stand 99: 17-22, 1999.*
Lipscomb et al. Dendritic cells: immune regulators in health and disease. Physiol Rev 82: 97-130, 2002.*
Dallaporta et al. Plasma membrane potential in thymocyte apoptosis. J Immunol 162: 6534-6542, 1999.*
Furlong et al. Induction of apoptosis by valinomycin: mitochondrial permeability transition causes intracellular acidification. Cell Death Different 5: 214-221, 1998.*
Gwag et al. Calcium ionophores can induce either apoptosis or necrosis in cultured cortical neurons. Neuroscience. 90(4):1339-1348, 1990.*
Sigma Chemical Company Catalog. "Ionophores", pp. 587-589, 1995.*
Calbiochem Catalog. 2000-2001. "Ionophores", pp. 1, 91, 208, 262, 310, 369, 403, 412, 483, 486, 520, 554, 912.*
Bakker et al. NK cell activation: distinct stimulatory pathways counterbalancing inhibitory signals. Hum Immunol. 61(1):18-27, 2000.*
Aiba et al. Dendritic cell activation induced by various stimuli, e.g. exposure to microorganisms, their products, cytokines, and simple chemicals as well as adhesion to extracellular matrix. J Dermatol Sci. 20(1):1-13, 1998.*
Xaus et al. Molecular mechanisms involved in macrophage survival, proliferation, activation or apoptosis. Immunobiology. 204(5):543-550, 2001.*
Kamath et al. Platelet activation: assessment and quantification.Eur Heart J. 22(17):1561-1571, 2001.*

(Continued)

*Primary Examiner*—Elizabeth Kemmerer
*Assistant Examiner*—Bridget E. Bunner
(74) *Attorney, Agent, or Firm*—Patterson, Thuente, Skaar & Christensen, P.A.; Peter S. Dardi

(57) ABSTRACT

A protocol of activating and administering human blood cells so that bone marrow histology and/or blood cell counts of patients suffering from aplastic anemia approach normal. The protocol includes culturing the blood cells in the presence of a cytokine and an ionophore. It is emphasized that this abstract is provided to comply with the rules requiring an abstract that will allow a searcher or other reader to quickly ascertain the subject matter of the technical disclosure. It is submitted with the understanding that it will not be used to interpret or limit the scope or meaning of the claims. 37 C.F.R. § 1.72(b).

21 Claims, 2 Drawing Sheets

OTHER PUBLICATIONS

Stewart et al. Vascular endothelial cell activation in models of vascular and glomerular injury. Kidney Int Suppl. 45:S37-44, 1994.*

Erdahl et al. Ca2+ transport properties of ionophores A23187, ionomycin, and 4-BrA23187 in a well defined model system. Biophys J 66: 1676-1693, 1994.*

Abramov et al. Actions of ionomycin, 4-BrA23187 and a novel electrogenic Ca2+ ionophore on mitochondria in intact cells. Cell Calcium 33: 101-112, 2003.*

Bedrosian et al., "Granulocyte-Macrophage Colony-Stimulating Factor, Interleukin-2, and Interleukin-12 Synergize With Calcium Ionophore to Enhance Dendritic Cell Function," Journal of Immunotheraphy, May-Jun. 2000, vol. 23, No. 3, pp. 311-320.

Chopra et al., "Interleukin 2, Interleukin 2 Receptor, and Interferon-yamma Synthesis and mNRA Expression in Phorbol Myristate Acetate and Calcium Ionophore A23187-Simulated T Cell From Elderly Humans," Clinical Immunology and Immunopathology, Nov. 1989, vol. 53, pp. 297-308.

Nobrega et al., "Naturally Activated and Resting T Cells Differ in Their Activation Requirements For Growth and Secretory Activities," Cellular Immunology, Jan. 1990, vol. 125, No. 1, pp. 120-129.

Rodriguez et al., "Regulation of Apoptosis in Interleukin-3-Dependent Hemopoietic Cells by Interleukin-3 and Calcium," The EMBO Journal, 1990, vol. 9, pp. 2997-3002.

Cooley et al., "Cytokine Activity after human bone marrow transplantation," British Journal of Haematology, vol. 73, No. 3, pp. 341-347, 1989.

Czerniecki et al., "Calcium Ionophore-Treated Peripheral Blood Monocytes and Dendritic Cells Rapidly Display Characteristics of Activated Dentritic Cells," Journal of Immunology, vol. 159, No. 8, pp. 3823-3837, Oct. 15, 1997.

Faries et al., "Calcium Signaling inhibits interleukin-12 production and activates $CD83^+$ dendritic cells that induce Th2 cell development," Blood, vol. 98, No. 8, pp. 2489-2497, Oct. 15, 2001.

Koski et al., "Calcium Ionophore-Treated Myeloid Cells Acquire Many Dendritic Cell Characteristics Independent of Prior Differentiation State, Transformation Status, or Sensitivity to Biologic Agents," Blood, vol. 94, No. 4, pp. 1359-1371, Aug. 15, 1999.

Roros et al., "Calcium ionophore and cytokine treatment of human peripheral blood myeloid cells produces dendritic cells with an enhanced abaility to sensitize autologous $CD8^+$ T cells to tumor antigens in a single culture stimulation," Proceedings of the annual meeting of the American Association for Cancer Research, New York, NY, vol. 38, pp. 631, Apr. 12, 1997.

Westers et al., "A23187/IL-4 Cultural Leukemic Dendritic Cells Stimulate Autologous T Cell-Mediated Apoptosis of Acute Myeloid Leukemic Blasts," Blood, vol. 98, No. 11 Part 1, pp. 121a, Nov. 16, 2001.

Bagby, "Production of Multi Lineage Growth Factors by Hematopoietic Stromal Cells: An Intercellular Regulatory Network Involving Mononuclear Phagocytes and Interleukin-1," Blood Cells, 13, pp. 147-159, 1987.

Champlin et al., "Treatment of Refactory Aplastic Anemia With Recombinant Human Granulocyte-Macrophage-Colony-Stimulating Factor," Blood, vol. 73, No. 3, pp. 694-699, Feb. 15, 1989.

Ettinghausen et al., "Hematologic Effects of Immunotherapy With Lymphokine-Activated Killer Cells and Recombinant Interleukin-2 in Cancer Patients," Blood, vol. 69, No. 6, pp. 1654-1660, Jun. 1987.

Ferrara et al., "Graft-Versus-Host Disease," The New England Journal of Medicine, Mechanisms of Disease, vol. 324, No. 10, pp. 667-674, Mar. 7, 1991.

Fibbe et al., "Human Fibroblasts Produce Granulocyte-CSF, Macrophage-CSF, and Granulocyte-Macrophage-CSF Following Stimulation by Interleukin-1 and Poly(R1). Poly(rC)," Blood, vol. 72, No. 3, pp. 860-866, Sep. 1988.

Fujimori et al., "Effect of Lymphokine-Activated Killer Cell Fraction on the Development of Human Hematopoietic Progenitor Cells," Cancer Res, vol. 48, No. 3, pp. 534-538, Feb. 1, 1988 (abstract only).

Ganser et al., "Effect of Recombinant Human Interleukin-3 in Patients With Normal Hematopoiesis and in Patients With Bone Marrow Failure," Blood, vol. 6, No. 4, pp. 666-676, Aug. 15, 1990.

Guinan et al., A Phase I/II Trial of Recombinant Granulocyte-Macrophage Colony-Stimulating Factor for Children With Aplastic Anemia, Blood, vol. 76, No. 6, pp. 1077-1082, Sep. 15, 1990.

Halpérin et al., "Severe Acquired Aplastic Anemia in Children: 11-Year Experience With Bone Marrow Transplantation and Immunosuppressive Therapy," American Journal of Pediatric Hematololy/Oncology, vol. 11, No. 3, pp. 304-309, 1989.

Hunt et al., "Lanthaide-Ion Transport Across Phospholipid Vesicular Membranes: A Comparison of Alamethicin 30 and A23187 Using $^1$H-NMR Spectroscopy," Bioscience Reports 2, pp. 921-928, 1982.

Hyono et al., "Fluorescence Energy Transfer Between Ionophore, A23187, and Membrane Proteins of Isolated Outer and Cytoplasmic Membranes of a Gram-Negative," Biochimica et Biophysica Acta, 813, pp. 111-116, 1985.

Kalf et al., "p-Benzoquinone, a Reactive Metabolite of Benzene, Prevents the Processing of Pre-interleukins-1α and -1β to Active Cytokines by Inhibition of the Processing Enzymes, Calpain, and Interluekin-1β Converting Enzyme," Environmental Health Perspectives, vol. 104, Supp. 6, pp. 1251-1256, Dec. 1996.

Kojima et al., "Treatment of Aplastic Anemia in Children With Recombinant Human Granulocyte-Colony Stimulating Factor," Blood, vol. 77, No. 5, pp. 937-941, Mar. 1, 1991.

Kolber et al., "Fluorescence Study of the Divalent Cation-Transport Mechanism of Ionophore A23187 in Phospholipid Membranes," Biophysical Society, vol. 36, pp. 369-391, Nov. 1981.

Jones et al., "Growth Factors in Haemopoiesis," Baillieres Clin Haematol, vol. 2, No. 1, pp. 83-111, Jan. 1989 (abstract only).

Laughlin et al., "Hematopoietic Recovery Following High-Dose Combined Alkylating-Agent Chemotherapy and Autologous Bone Marrow Support in Patients in Phase-I Clinical Trials of Colony-Stimulating Factors: G-CSF, GM-CSF, IL-1, IL-2, M-CSF," Ann Hematol, vol. 67, No. 6, pp. 267-276, Dec. 1993 (abstract only).

Liu et al., "Cellular Interactions in Hemopoiesis," Blood Cells, 13, pp. 101-110, 1987.

Niculescu et al., "Inhibition of the Conversion of Pre-interleukins-1α and 1β To Mature Cytokines by p-Benzoquinone, a Metabolite of Benzene," Chemico-Biological Interactions, 98, pp. 211-222, 1995.

Nimmer et al., "A Phase I/II Study of Interleukin-3 in Patients With Aplastic Anemia and Myelodysplasia," Experimental Hematology, 22, pp. 875-880, 1994.

Passweg et al., "Bone Marrow Transplantation for Severe Aplastic Anemia: Has Outcome Improved?," Blood, vol. 90, No. 2, pp. 858-864, Jul. 15, 1997.

Rosenfeld et al., "Intensive Immunosuppression With Antithymocyte Globulin and Cyclosporine as Treatment for Severe Aplastic Anemia," Blood, vol. 85, No. 11, pp. 3058-3065, Jun. 1, 1995.

Setti et al., "The Induction of Distinct Cytokine Cascades Correlates With Different Effects of Granulocyte-Colony Stimulating Factor and Granulocyte/Macrophage-Colony-Stimulating Factor on the Lymphocyte Compartment in the Course of High-Dose Chemotherapy for Breast Cancer," Cancer Immunol Immunother, vol. 48, No. 6, pp. 287-296, Sep. 1999 (abstract only).

Socié et al., "Malignant Tumors Occurring After Treatment of Aplastic Anemia," New England Journal of Medicine, vol. 329, No. 16, pp. 1152-1157, Oct. 14, 1993.

Sonoda et al., "Multilineage Response in Aplastic Anemia Patients Following Long-Term Administration of Filgrastim (Recombinant Human Granulocyte Colony Stimulating Factor)," Stem Cells, 11, pp. 543-554, 1993.

Young et al., "The Pathophysiology of Acquired Aplastic Anemia," New England Journal of Medicine, Mechanisms of Disease, vol. 336, No. 19, pp. 1365-1372, May 8, 1997.

Young et al., "The Treatment of Severe Acquired Aplastic Anemia," Blood, vol. 85, No. 12, pp. 3367-3377, Jun. 15, 1995.

* cited by examiner

STIMULATION OF HEMATOPOIESIS BY EX VIVO ACTIVATED IMMUNE CELLS

BACKGROUND OF THE INVENTION

1. Field of the Invention

This invention relates to therapies for aplastic anemia, anemia and thrombocytopenic purpura. In particular, this invention relates to ex vivo activated immune cells as therapies for aplastic anemia, anemia and thrombocytopenic purpura. Furthermore, the invention relates to approaches to activate cells and corresponding cell culture approaches.

2. Background

Aplastic anemia is a disease characterized by ineffective hematopoiesis. Patients have varying degrees of abnormalities in production of all blood cell types. Although in most cases, the cause of the disease is unknown, radiation, benzene-based compounds, viruses (e.g., hepatitis), environmental toxins, and over the counter and prescription medications have been suspected to damage bone marrow, thereby leading to apoptosis of marrow stem cells. Regardless of the underlying causes, patients show similar clinical manifestations and disease progression courses. Aplastic anemia affects primarily young man and older persons of both the genders. Annually, two to six per million worldwide develop this disorder, with a prevalence of incidences in the Orient as compared to Europe or the United States. Several causal phenomena are hypothesized for aplastic anemia: congenital, pregnancy, viral, and drugs and chemicals.

The most frequently cited causal agent of aplastic anemia is drugs or chemical exposure. Some agents, such as chloramphenicol, benzene, ionizing radiation, and antineoplastic agents, cause an aplasia that is dose-related in severity from person-to-person. In these cases, marrow recovery usually occurs after withdrawal of the causal agent. Other agents, including pesticides and some anticonvulsants and antimicrobials, cause a reaction which is not dose-related and, therefore, cannot be predicted with hematological monitoring during administration. During administration of drugs, aplasias may occur even after cessation of drug therapy. In contrast to patients with idiopathic aplastic anemia, those with drug or toxin exposure exhibit similar clinical and demographic characteristics, have a similar prognosis, and a more-or-less uniform response to therapy.

In the case of benzene-induced aplastic anemia, mild to moderate disease symptoms usually disappear after patients cease being exposed to benzene. However, for patients with severe bone marrow failure or who continually need blood transfusions, effective and safe treatment has not often been heretofore available. To date, bone marrow transplantation is the only known cure.

Mild aplastic patients are often treated with as little therapy as possible. The rationale for minimum treatment for mildly aplastic patients is to remove the causal agent, thereby enabling spontaneous recovery. In young patients with severe anemia, bone marrow transplantation with an HLA-matched donor is the treatment of choice. Bone marrow transplantation effects complete remission in nearly 80% of cases. However, survival decreases to 10–20% when the donor and recipient are mismatched at two or more loci. Complications associated with transplantation include graft rejection, acute or chronic graft-versus-host disease, infection, and other miscellaneous organ specific damage. Marrow transplant recipients also have an increased long-term risk for developing subsequent solid tumors.

SUMMARY OF THE INVENTION

The present inventor has investigated using cultured (activated) blood cells for treating patients with blood deficiencies, such as anemia, aplastic anemia and/or thrombocytopenic purpura. In one embodiment of the invention, a quantity of blood cells effective to treat blood deficiencies when injected into a patient is provided. The quantity of blood cells may be cultured in the presence of a cytokine and an ionophore. The cytokine and ionophore may be present in effective concentrations. The cytokine may comprise interleukin-2 and macrophage-colony stimulating factor. The ionophore may comprise A23187.

In another embodiment, the present invention provides a process of treating blood deficiencies in a patient, the treatment comprising administering ex vivo cultured blood cells to the patient. A therapeutically effective amount of blood cells may be administered to the patient. The blood cells may be autologous to the patient, allogeneic to the patient, or from an immunologically acceptable owner. The blood cells may further be cultured in the presence of a cytokine and an ionophore. The cytokine and ionophore may be present in effective amounts.

In yet another embodiment, the present invention provides a method of culturing blood cells, the method comprising culturing the blood cells in the presence of a cytokine and an ionophore. The blood cells may be cultured in the presence, for example, of effective amounts of the cytokine and ionophore; may be cultured in a medium which may or may not comprise mammalian serum; may be cultured for a period, for example, between about 2 and 200 hours or longer; and may be cultured at a temperature, for example, between about 30 and 42 degrees C. The cytokine may include interleukin-2 and/or granulocyte macrophage-colony stimulating factor. The ionophore may include A23187.

DETAILED DESCRIPTION

Figure 1:
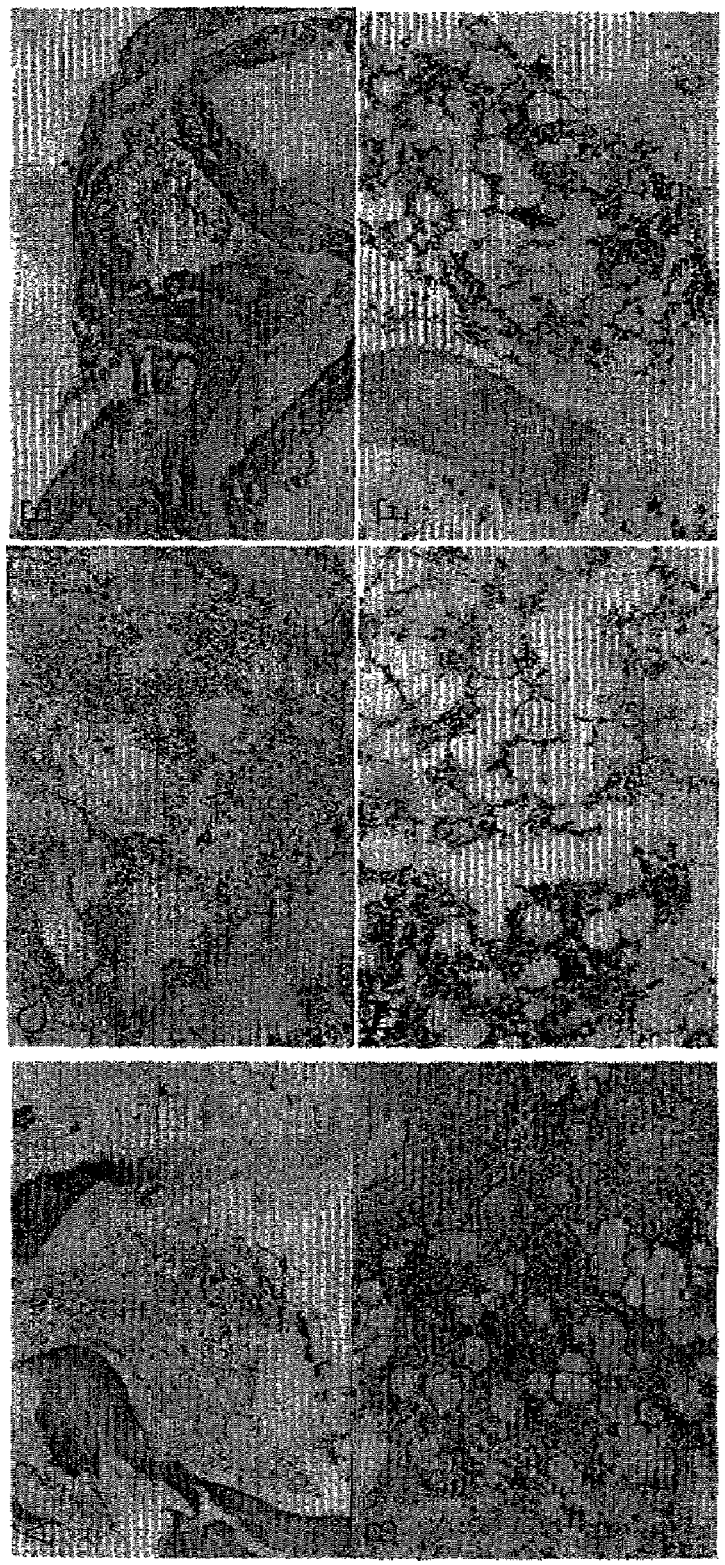
FIG. 1 shows low-power views of H&E stained bone marrow biopsies from three patients responsive to the present therapy. The views labeled as A, C and E are marrows from patients before treatment. In these views, early empty and impaired marrows implicate severe aplastic anemia. In the views denoted as B, D and F, the marrows are from the same patients after treatment. These marrows show much improved distribution and cellularity.

The present invention includes a therapy of administering a therapeutically effect amount of ex vivo cultured blood cells to patients afflicted with blood deficiencies, such as anemia, aplastic anemia and thrombocytopenic purpura. The term "therapeutically effective amount" is intended to include a sufficient quantity of the present activated blood cells to effect a statistically significant increase in blood cell counts when administered to a patient with blood deficiencies, i.e., a significantly low concentration of a natural blood component, such as red blood cells, white blood cells, platelets and other factors produced by the bone marrow and cells generated from the bone marrow. The cultured blood cells may be either from the patient or from an immunologically acceptable donor. One protocol for activating blood cells via ex vivo culture includes obtaining a blood sample (e.g., 10–100 ml) from the patient, or an immunologically acceptable donor, separating blood cells from the blood sample, and culturing the separated blood cells. An "immunologically acceptable donor" is a person having tissues, to include blood cells, that do not have medically unacceptable levels of recipient reactions (e.g., hemolytic anemia, heart failure, renal failure). The blood cells may be separated from blood sera by protocols such as by centrifugation. The separated blood cells are then cultured under sterile conditions in a medium with one or more of a cytokine (to include cell stimulating factors) and an ionophore. The separated blood cells may be cultured in the media as specified above, for example, for periods between of greater than about 1 hour, in other embodiments between about 10 and 200 hours, between about 20 and 80 hours, or between about 30 and 60 hours and at a temperature, for example, between about 30 and 42 degrees C., in other embodiments between about 32 and 40 degrees C., or between about 37 and 38 degrees C. or any range subsumed therein. A person of ordinary skill in the art will recognize that other ranges of periods and temperatures within these explicit ranges are contemplated, and are within the present disclosure.

Blood deficiencies can be treated by the approaches described herein. In general, the blood deficiencies involve a reduced concentration of blood components that originate from the bone marrow or from products, such as specific cell types, from the bone marrow. Blood deficiencies include, for example, anemia, aplastic anemia and thrombocytopenic purpura. Anemia can be considered broadly as a deficiency of a blood component or, in some contexts, as a deficiency of red blood cells. Aplastic anemia is a deficiency of peripheral blood elements. Thrombocytopenic purpura, such as idiopathic thrombocytopenic purpura, involves a deficiency in platelet number. As a specific example, the discussion below describes aplastic anemia in some detail, although the treatment methods can be applicable more broadly.

After being cultured, the activated blood cells may be washed (e.g., twice with sterile saline solution). Therapeutically effective amounts of the activated blood cells are then administered to patients. One acceptable method of administering the activated blood cells is intravenously. While the activated cells may be administered in a single dose, portions of the activated blood cells may also be administered over a period of time. For example, doses of the present activated blood cells may be administered to patients once per week for a period of four weeks. However doses of the present activated blood cells may be administered to patients at intervals of, for example, one-half week, ten days, 14 days, 21 days, other intermediate periods, or other effective periods. Moreover, the intervals may vary during the course of the treatment. For example, initially blood cell doses may be administered at daily, twice a week, weekly, and/or bin-weekly intervals. The dosages can be, for example, between about $1 \times 10^5$ to about $2 \times 10^8$ cells per treatment, which may depend on the patient's age and condition. The total time required for treatment (e.g., administering the present activated blood cells) may depend on the amount of activated blood cells available and patient response. Patient response can be measured, for example, in terms of return to normal blood cell counts and/or marrow histology as well as an overall improvement in health. Obviously, blood samples can be drawn from patients repeatedly during or after the initial treatment period so that additional activated blood cells can be obtained for further treatments. Furthermore, activated blood cells from an immunologically acceptable donor can be administered initially or administered for the entire duration of the treatment. Alternatively, blood cells from the patient, activated by the present protocol, may be administered after blood cells from an immunologically acceptable donor are initially administered.

The most current definition of severe aplastic anemia is marked pancytopenia with at least two of the following: 1) granulocytes less than 500/microliter, 2) platelets less than 20,000/microliter, 3) anemia with corrected reticulocyte count less than 1%, plus markedly hypoplastic marrow depleted of hematopoietic cells. Moderate aplastic anemia generally involves a hypocellular bone marrow and cytopenia in at least two cell lines not in the severe range. Onset is insidious and the initial complaint may be progressive fatigue and weakness due to the anemia, followed in some cases by hemorrhage. The hemorrhage is usually from the skin and mucosal linings, due to thrombocytopenia. Infection is rare despite the severe neutropenia. Physical examination reveals pallor and possibly bruising or petechiae. Aplastic anemia patients exhibit no lymphadenopathy or splenomegaly. Fever may or may not be present. Peripheral blood assays show pancytopenia. The presence of immature red and white blood cells strongly argues against aplastic anemia.

Red blood cells may be mildly macrocytic due to increased erythropoietic stress and they usually are normocytic and normochromic. The corrected reticulocyte count is very low or zero, indicating a lack of erythropoiesis. Bleeding time may be prolonged even with normal coagulation parameters. Patients have an increased serum iron and a normal transferrin, resulting in an elevated transferrin saturation. Plasma iron clearance is decreased due to a reduction in erythropoiesis. Bone marrow aspirate may be dry. But a biopsy can show severe hypocellular or aplastic marrow with fatty replacement. Because there have been cases in which the initial marrow biopsy exhibited hypercellularity, more than one biopsy may be necessary for accurate diagnosis. A severe depression can be noted in all hematopoietic progenitor cells, including myeloid, erythroid, pluripotent cell lines, and megakaryocytes. Diagnosis generally is based on finding the classic triad of anemia, neutropenia, and thrombocytopenia in both blood and bone marrow specimens. X-rays may be needed to rule out bone lesions or neoplastic infiltrates. Magnetic resonance imaging has been useful in clearly defining hypoplastic marrow. Since the diagnosis is one of exclusion, all other causes of pancytopenia and other lab findings are usually ruled out before aplastic anemia can be diagnosed.

The basic defect in aplastic anemia is failure of production of all cell lines. Possible mechanisms of the pathogenesis of aplastic anemia include 1) defective or absent hematopoietic stem cells, 2) abnormal bone marrow microenvironment, 3) abnormal regulatory cells, and 4) suppression of hematopoiesis by immunologic cells.

While the pathophysiology of the disease is not yet completely clear, (Young et al., The pathophysiology of acquired aplastic anemia, N. Engl. J. Med. 1997; 336(19): 1365–1372 and Young et al., The treatment of severe acquired aplastic anemia, Blood. 1995; 85(12): 3367–3377) there is evidence to support the theory that aplastic anemia is an immune-mediated disease. Bone marrow transplantation and immunosuppressive therapy using combined antilymphocyte globulin and cyclosporine have been used for treatment (Rosenfeld et al., Intensive immunosuppression with antithymocyte globulin and cyclosporine as treatment for severe aplastic anemia, Blood 1995; 85(11): 3058–3065 and Halperin et al., Severe acquired aplastic anemia in children: 11-year experience with bone marrow transplantation and immunosuppressive therapy, Am. J. Pediatr. Hematol. Oncol. 1989; 11(3): 304–309). However, the therapy of immune suppression often has undesirable and severe side effects. Moreover, hematopoietic growth factors such as granulocyte colony-stimulating factor (Kojima et al., Treatment of aplastic anemia in children with recombinant human granulocyte-colony stimulating factor, Blood 1991; 77(5): 937–941 and Sonoda et al., Multilineage response in aplastic anemia patients following long-term administration of filgrastim (recombinant human granulocyte colony stimulating factor), Stem Cells 1993; 11: 543–554), granulocyte macrophage colony-stimulating factor (Champlin et al., Treatment of refactory aplastic anemia with recombinant human granulocyte-macrophage-colony-stimulating factor, Blood 1989; 73(3): 694–699 and Guinan et al., A phase I/II trial of recombinant granulocyte-macrophage colony-stimulating factor for children with aplastic anemia, Blood 1990; 76(6): 1077–1082), and Interleukin-3 (Ganser et al., Effect of recombinant human interleukin-3 in patients with normal hematopoiesis and in patients with bone marrow failure, Blood 1990; 76(4): 666–676 and Nimer et al., A phase I/II study of interluekin-3 in patients with aplastic anemia and myelodysplasia, Exp. Hematol. 1994; 22: 875–880) have provided only limited and transient effects.

Many patients respond to immunosuppressive therapy and there are abnormal levels of various immune molecules in aplastic patients. For instance, Interleukin-1, produced by macrophages, natural killer cells, B lymphocytes, and endothelial cells, plays a central role in both immune responses and regulation of hematopoiesis by inducing the release of erythroid and multipotent colony-stimulating factors from marrow stromal cells, regulating early progenitor cells and stimulating stem cell recovery following induced myelosuppression. Immune dysregulation in aplastic anemia consists of decreased natural killer cell activity, increased numbers of activated T suppressor cells and abnormal production of Interleukin-2 and gamma-Interferon.

Natural killer cells are large granular lymphocytes which lyse tumor cells or virus-infected target cells upon direct contact. Natural killer cells also produce gamma-interferon, Interleukin-2, and induces colony-stimulating activity. These cells may inhibit myeloid and erythroid colony formation under certain conditions. For instance, when exogenous growth factors are absent from a culture, natural killer cells normally produce cytokines and support hematopoiesis. However, optimal conditions induce natural killer cells to inhibit hematopoiesis. Natural killer cell activity in aplastic anemia patients returns to normal after hematopoietic recovery.

Gamma-Interferon is produced by activated lymphocytes and suppresses hematopoiesis. Although aplastic patients show an overproduction of gamma-Interferon, levels of gamma-Interferon decrease in response to immunosuppression. Interferons are potent inhibitors of hematopoietic colony formation—both through direct action on progenitor cells and indirect effects via accessory immune system cells.

Tumor necrosis factor-alpha is another cytokine which is in excess in aplastic anemia. It functions to inhibit colony growth of the normal hematologic progenitors. High tumor necrosis factor-alpha values correlate with decreased platelet, hemoglobin, and leukocyte counts. Tumor necrosis factor-alpha and gamma-Interferon may act synergistically to suppressor hematopoiesis.

Aplastic anemia patients produce gamma-Interferon and tumor necrosis factor-alpha in excess, show an inverted helper:suppressor T cell ratio, and have predominantly T suppressor cells in the bone marrow. These cells may mediate suppression of hematopoiesis via cytokine production. The bone marrow also has a higher proportion of cytotoxic T cells than peripheral blood. The clinical relevance of immune dysfunction is suggested by a decrease in activated lymphocytes following successful immunosuppressive therapy.

Mechanisms for acquired aplastic anemia in general, and mechanisms for benzene-induced aplastic anemia in particular, are not well understood. Nonetheless, both types of aplastic anemia share considerable similarities with respect to pathophysiology and clinical manifestations. There are presently two hypotheses to explain the mechanism of aplastic anemia, direct damage and immune-mediated. Both hypotheses are supported by data from experimental and clinical studies. Direct damage to bone marrow cells is thought to be responsible for temporary and reversible bone marrow failure following cytotoxic chemotherapy and radiotherapy. Immune-mediated bone marrow failure is more difficult to cure. In the case of benzene-induced aplastic anemia, the disease seems to be associated with both mechanisms. Evidence of direct damage to bone marrow cells is supported by the studies indicating that benzene is involved in inhibiting a number of biochemical processes of bone marrow cells. Specifically, benzene has been shown to damage stromal macrophages in bone marrow, thereby leading to deficient interleukin-1 production (Niculescu et al., Inhibition of the conversion of pre-interleukins-1[alpha] and 1[beta] to mature cytokines by p-benzoquinone, a metabolite of benzene, Chemico-Biological Interactions; 1995; 98: 211–222 and Kalf et al., p-benzoquinone, a reactive metabolite of benzene, prevents the processing of pre-interleukins-1[alpha] and -1 [beta] to active cytokines by inhibition of the processing enzymes, calpain, and interluekin-1 [beta] converting enzyme, Environmental Health Perspectives; 1996; 104 (suppl. 6): 1251–1256). Interleukin-1 is considered important for growth and differentiation of stem cells (Bagby, G. C., Production of multi lineage growth factors by hematopoietic stromal cells: an intercellular regulatory network involving mononuclear phagocytes and interleukin-1, Blood Cells 1987; 13:147–159 and Fibbe et al., Human fibroblasts produce granulocyte-CSF, macrophage-CSF and granulocyte-macrophage-CSF following stimulation by interleukin-1 and poly(r1).poly(rC), Blood 1988; 72(3): 860–866). However, there has been no report of prolonged response to treatments of hematopoietic growth factors, including interleukin-1.

Medium

Suitable media used in ex vivo activation provide essential nutrients for blood cells. These media generally comprise, for example, inorganic salts, amino acids, vitamins, and other compounds all in forms which can be directly utilized by blood cells. By way of illustration and not limitation, one suitable medium is RPMI 1640. However, other media, such as serum-free media AIM-V, will support blood cells in culture may be suitable as well. The medium may be supplemented with a mammalian serum, e.g., fetal bovine serum at levels between about 0.1 and 50%, between about 1 and 40%, or between about 5% and 15%, of the medium, by weight. One suitable formulation of RPMI, designated as a modified RPMI 1640 and available under catalog number 30-2001 from American Type Culture Collection, has the following ingredients:

| Inorganic Salts | (g/liter) |
|---|---|
| Ca(NO$_3$)$_2$.4H$_2$O | 0.10000 |
| MgSO$_4$ (anhydrous) | 0.04884 |
| KCl | 0.40000 |
| NaHCO$_3$ | 1.50000 |
| NaCl | 6.00000 |
| Na$_2$HPO$_4$ (anhydrous) | 0.80000 |

| Amino Acids | (g/liter) |
|---|---|
| L-Arginine (free base) | 0.20000 |
| L-Asparagine.H$_2$O | 0.05682 |
| L-Aspartic Acid | 0.02000 |
| L-Cystine.2HCl | 0.06520 |
| L-Glutamic Acid | 0.02000 |
| L-Glutamine | 0.30000 |
| Glycine | 0.01000 |
| L-Histidine (free base) | 0.01500 |
| Hydroxy-L-Proline | 0.02000 |
| L-Isoleucine | 0.05000 |
| L-Leucine | 0.05000 |
| L-Lysine.HCl | 0.04000 |
| L-Methionine | 0.01500 |
| L-Phenylalanine | 0.01500 |
| L-Proline | 0.02000 |
| L-Serine | 0.03000 |
| L-Threonine | 0.02000 |
| L-Tryptophan | 0.00500 |
| L-Tyrosine.2Na.2H$_2$O | 0.02883 |
| L-Valine | 0.02000 |

| Vitamins | (g/liter) |
|---|---|
| D-Biotin | 0.00020 |
| Choline Chloride | 0.00300 |
| Folic Acid | 0.00100 |
| myo-Inositol | 0.03500 |
| Nicotinamide | 0.00100 |
| p-Amino Benzoic Acid | 0.00100 |
| D-Pantothenic Acid (hemicalcium) | 0.00025 |
| Pyridoxine.HCl | 0.00100 |
| Riboflavin | 0.00020 |
| Thiamine.HCl | 0.00100 |
| Vitamin B-12 | 0.000005 |

| Other | (g/liter) |
|---|---|
| D-Glucose | 4.50000 |
| Glutathione (reduced) | 0.00100 |
| HEPES | 2.38300 |
| Phenol Red, Sodium Salt | 0.00500 |
| Sodium Pyruvate | 0.11000 |

1. Cytokines. One or more cytokines may be used to activate blood cells when cultured in the presence thereof. Cytokines are small proteins (usually in the range of 5–20 kD) that are released by cells and have specific effects on cell-cell interaction, communication, and behavior of other cells. Usually included as cytokines, are interleukins, lymphokines and signaling molecules such as tumor necrosis factor (TNF) and interferons. While natural cytokines can be used, recombinant produced cytokines produced, for example, by established nucleic acid expression systems are also contemplated. As such, modified and mutated forms of natural cytokines that maintain function can also be used. Exemplary cytokines, which may be suitable for some embodiments of the present invention, include:

A. Interleukins. A variety of naturally occurring polypeptides that affect functions of specific cell types and are found in small quantities. They are secreted regulatory proteins produced by lymphocytes, monocytes and various other cells and are released by cells in response to antigenic and non-antigenic stimuli. The interleukins, of which there are 16 identified to date, modulate inflammation and immunity by regulating growth, mobility and differentiation of lymphoid and other cells. Interleukins may be present in concentrations between about 10 and 50,000 IU/ml, about 100–5,000 IU/ml, or about 100–1,000 IU/ml. Alternatively an effective concentration of interleukins may be present. An effective concentration of interleukins is any concentration at which blood cells are actived by the present protocol.

i. Interleukin-1 (IL-1). IL-1 is a soluble protein (17 kD: 152 amino acids) secreted by monocytes, macrophages or accessory cells involved in the activation of both T lymphocytes and B lymphocytes and potentiates their response to antigens or mitogens. Biological effects of IL-1 include the ability to replace macrophage requirements for T-cell activation, as well as affecting a wide range of other cell types. At least two IL-1 genes are known and alpha and beta forms of IL-1 are recognized. IL-1 is released early in an immune system response by monocytes and macrophages. It stimulates T-cell proliferation and protein synthesis. Another effect of IL-1 is to cause fever.

ii. Interleukin-2 (IL-2). IL-2 is a hormone-like substance released by stimulated T lymphocytes. IL-2 causes activation and differentiation of other T lymphocytes independently of antigen. IL-2 stimulates the growth of certain disease-fighting blood cells in the immune system and is secreted by Th1 CD4 cells to stimulate CD8 cytotoxic T lymphocytes. IL-2 also increases the proliferation and maturation of CD4 cells themselves.

iii. Interleukin-3 (IL-3). IL-3 is a product of mitogen activated T-cells. IL-3 is a colony stimulating factor for bone marrow stem cells and mast cells. IL-3 is considered one of the hematopoietic colony stimulating factors.

iv. Interleukin-4 (IL-4). IL-4 is a soluble cytokine factor produced by activated T lymphocytes that promotes antibody production by causing proliferation and differentiation of B-cells. IL-4 induces the expression of class II major histocompatibility complex and fc receptors on B-cells. IL-4 also acts on T lymphocytes, mast cell lines, and several other hematopoietic lineage cells including granulocyte, megakaryocyte, and erythroid precursors, as well as macrophages.

v. Interleukin-5 (IL-5). IL-5 is a factor promoting eosinophil differentiation and activation in hematopoiesis. It also triggers activated B-cells for a terminal differentiation into Ig-secreting cells.

vi. Interleukin-6 (IL-6). IL-6 stimulates the growth and differentiation of human B-cells and is also a growth factor for hybridomas and plasmacytomas. It is produced by many different cells including T-cells, monocytes, and fibroblasts. IL-6 is a single chain 25 kD cytokine originally described as a pre B-cell growth factor, now known to have effects on a number of other cells including T-cells which are also stimulated to proliferate.

vii. Interleukin-7 (IL-7). IL-7 is a hematopoietic growth factor that promotes growth of B-cell precursors and is also co-mitogenic with interleukin-2 for mature T-cell activation. IL-7 is produced by bone marrow stromal cells.

viii. Interleukin-8 (IL-8). IL-8 is a cytokine that activates neutrophils and attracts neutrophils and T lymphocytes. IL-8 is released by several cell types including monocytes, macrophages, T lymphocytes, fibroblasts, endothelial cells, and keratinocytes by an inflammatory stimulus. IL-8 is a member of the beta-thromboglobulin superfamily and structurally related to platelet factor 4.

ix. Interleukin-9 (IL-9). IL-9 is a cytokine produced by T-cells, particularly when mitogen stimulated. IL-9 stimulates the proliferation of erythroid precursor cells (BFUE) and is thought to be a regulator of hematopoiesis. IL-9 may act synergistically with erythropoietin. The IL-9 receptor belongs to the hemopoietic receptor super family. IL-9 has been shown to enhance the growth of human mast cells and megakaryoblastic leukaemic cells as well as murine helper T-cell clones. Il-9 is a glycoprotein that is derived from T-cells and maps to human chromosome 5.

x. Interleukin-10 (IL-10). IL-10 is a factor produced by Th2 helper T-cells, some B-cells and LPS activated monocytes. It is a coregulator of mast cell growth.

xi. Interleukin-11 (IL-11). IL-11 is a pleiotropic cytokine, originally isolated from primate bone marrow stromal cell line, that has the ability to modulate antigen-specific antibody responses, potentiate megakaryocytes, and regulate bone marrow adipogenesis. IL-11 stimulates T-cell dependent B-cell maturation, megakaryopoiesis, and various stages of myeloid differentiation.

xii. Interleukin-12 (IL-12). IL-12 is a 75 kD heterodimeric cytokine composed of disulfide-bonded 40 kD and 35 kD subunits that was originally identified by its ability to induce cytotoxic effector cells in synergy with less than optimal concentrations of interleukin-2. IL-12 is released by macrophages in response to infection and promotes the activation of cell-mediated immunity. Specifically, IL-12 triggers the maturation of Th1 CD4 cells, specific cytotoxic T lymphocyte responses, and an increase in the activity of NK cells. Consequently, IL-12 is the initiator of cell-mediated immunity. It enhances the lytic activity of NK cells, induces interferon production, stimulates the proliferation of activated T-cells and NK cells. Is secreted by human B lymphoblastoid cells (NC 37).

xiii. Interleukin-13 (IL-13). IL-13 is a T lymphocyte-derived cytokine that produces proliferation, immunoglobulin isotype switching, and immunoglobulin production by immature B-lymphocytes. IL-13 is produced by activated T-cells, inhibits IL-6 production by monocytes, and also inhibits the production of other pro-inflammatory cytokines such as TNF, IL-1, and IL-8. IL-13 stimulates B-cells. The gene for IL-13 is located on human chromosome 5q in a gene cluster that also has the IL-4 gene.

xiv. Interleukin-14 (IL-14). IL-14 is a cytokine that induces B-cell proliferation, inhibits immunoglobulin secretion, and selectively expands certain B-cell subpopulations.

xv. Interleukin-15 (IL-15). IL-15 is a cytokine that stimulates the proliferation of T lymphocytes and shares biological activities with IL-2. Il–15 also can induce B lymphocyte proliferation and differentiation.

xvi. Interleukin-16 (IL-16). IL-16 is a cytokine produced by activated T lymphocytes that stimulates the migration of CD4-positive lymphocytes and monocytes.

B. Lymphokines. A lymphokine is a substance produced by a leucocyte that acts upon another cell. Examples are interleukins, interferon alpha, lymphotoxin (tumor necrosis factor alpha), granulocyte monocyte colony stimulating factor (GM-CSF).

i. Interferons (IFN) are a family of glycoproteins human cells which normally have a role in fighting viral infections by preventing virus multiplication in cells. Interferons may be present in the same concentrations as interluekins. Alternatively, effective concentrations of interferons may be present. Effective concentrations of interferons are contemplated to include any concentration at which blood cells are activated by the present protocol. IFN alpha is secreted by leucocytes and IFN gamma is secreted by fibroblasts after viral infection.

1. Interferon gamma is an interferon elaborated by T lymphocytes in response to either specific antigen or mitogenic stimulation.

2. Interferon alpha includes a number of different subtypes that are elaborated by leukocytes in response to viral infection or stimulation with double-stranded RNA. IFN-alpha-2A and -2B are protein products made by recombinant DNA techniques and are used as antineoplastic agents. Interferon-alpha is one of the type I interferons (interferon type I) produced by peripheral blood leukocytes or lymphoblastoid cells when exposed to live or inactivated virus, double-stranded RNA, or bacterial products. It is the major interferon produced by virus-induced leukocyte cultures and, in addition to its pronounced antiviral activity, causes activation of natural killer cells.

3. Interferon alfa-2a is a type I interferon consisting of 165 amino acid residues with lysine in position 23. This protein is produced by recombinant DNA technology and resembles interferon secreted by leukocytes. It is used extensively as an antiviral or antineoplastic agent.

4. Interferon alfa-2b is type I interferon consisting of 165 amino acid residues with arginine in position 23. This protein is produced by recombinant DNA technology and resembles interferon secreted by leukocytes. It is used extensively as an antiviral or antineoplastic agent.

5. Interferon beta is an interferon elaborated by fibroblasts in response to the same stimuli as interferon alpha. Interferon-beta is one of the type I interferons produced by fibroblasts in response to stimulation by live or inactivated virus or by double-stranded RNA. It is a cytokine with antiviral, antiproliferative, and immunomodulating activity.

6. Interferon-b2 (interleukin-6) is a cytokine that stimulates the growth and differentiation of human B-cells and is also a growth factor for hybridomas and plasmacytomas. It is produced by many different cells including T-cells, monocytes, and fibroblasts. INF-b2 is a single chain 25 kD cytokine originally described as a pre B-cell growth factor, now known to have effects on a number of other cells including T-cells, which are also stimulated to proliferate. INF-b2 is an inducer of acute phase proteins and a colony stimulating factor acting on mouse bone marrow.

7. Interferon gamma is elaborated by T lymphocytes in response to either specific antigen or mitogenic stimulation.

ii. Tumor necrosis factor (TNF) is a tumor-inhibiting factor present in the blood of animals exposed to bacterial lipopolysaccharide. TNF preferentially kills tumor cells in vivo and in vitro, causes necrosis of certain transplanted tumors in mice, and inhibits experimental metastases. Human TNF alpha is a protein of 157 amino acids and has a wide range of pro-inflammatory actions. TNF may be present in the same concentrations as interleukins. Alternatively, TNF may be present in an effective concentration. An effective concentration of TNF is an concentration at which blood cells are activated by the present protocol.

C. Cell Stimulating Factors. Activating blood cells in the presence of one or more cell stimulation factors may be efficacious in alleviating aplastic anemia in the context of the present invention. Cell stimulating factors are contemplated to include such substances as granulocyte colony-stimulating factor granulocyte macrophage-colony stimulating factor and macrophage-colony stimulating factor. Cell stimulating factors may be present in concentrations between about 10 and 50,000 IU/ml, between about 10 and 10,000 IU/ml, or between about 10 and 1000 IU/ml. Alternatively, an effective concentration of cell stimulating factors may be present. An effective concentration of cell stimulating factors is any concentration at which blood cells are activated by the present protocol.

1. Granulocyte colony-stimulating factor (G-CSF): G-CSF are glycoproteins synthesized by a variety of cells and are involved in growth and differentiation of hematopoietic stem cells. In addition, these factors stimulate the end-cell functional activity of stem cells.

2. Granulocyte-macrophage colony-stimulating factor (GM-CSF): GM-CSF is an acidic glycoprotein of 23 kD with internal disulfide bonds. GM-CSF is produced in response to a number of inflammatory mediators by mesenchymal cells present in the hemopoietic environment and at peripheral sites of inflammation. GM-CSF stimulates the production of neutrophilic granulocytes, macrophages, and mixed granulocyte-macrophage colonies from bone marrow cells and can stimulate the formation of eosinophil colonies from fetal liver progenitor cells.

3. Macrophage-colony stimulating factor (M-CSF): M-CSF is a cytokine synthesised by mesenchymal cells that stimulates pluripotent stem cells of bone marrow into differentiating towards the production of monocytes (mononuclear phagocytes). The compound stimulates the survival, proliferation, and differentiation of hematopoietic cells of the monocyte-macrophage series. It is a disulfide-bonded glycoprotein dimer with a mw of 70 kD and binds to a single class of high affinity receptor which is identical to the product of the c-fms proto-oncogene.

2. Ionophores. Ionophores are calcium or other cation specific reagents (such as polypeptrates) which can traverse a lipid bilayer and a lipid soluble. There are two classes of ionophores: carriers and channel formers. Carriers, like valinomycin, form cage-like structures around specific ions, diffusing freely through the hydrophobic regions of the bilayer. Channel formers, like gramicidin, form continuous aqueous pores through the bilayer, allowing ions to defuse therethrough. In addition to the foregoing, suitable ionophores for the present protocol may include A23187 (calcimycin), ionomycin, geldanamycin, monensin (Na-salt), nystatin, polymyxin-B sulfate, and rapamycin. It is believed that carriers, such as A23187, accumulate calcium cations in response to pH gradients. A23187 possesses a dissociating carboxylic acid group and catalyzes an electrically neutral exchange of protons for other cations across the membrane (Hyono et al., BBA 389, 34–46 (1985): Kolber and Haynes, Biophysics Journal, 36, 369–391 (1981); Hunt and Jones, Biosci. Rep., 2, 921–928 (1982)). Two molecules of A23187 are present as carboxylate anions, and are thus available to carry to protons, or equivalents, back across the membrane after releasing the transported divalent cation. If present, ionophores may be present in concentrations between about 1 and 10,000 ng/ml, between about 1 and 1000 ng/ml, or between about 10 and 500 ng/ml. Alternately, ionophores may be present in an effective concentration. An effective concentration of ionophores is any concentration at which blood cells are activated, but not over-activated, by the present protocol. Excessive concentrations of activating agents may not be effective in the treatment approaches described herein.

Use, Packaging and Distribution

The delivery of activated cells can provide a statistically significant improvement in clinical parameters of a patient. For example, the administration of cell activated as described herein can result in a statistically significant increase in white blood cell counts, red blood cell counts hemoglobin levels and platelet counts. In general, continuation of the treatment procedure as described herein can result in a return to normal blood levels. In some embodiments, after four treatments, the patient can have an increase in each of white blood cell counts, red blood cell counts and hemoglobin of at least about 20%, in other embodiments at least about 35% and in other embodiments at least about 50%. Similarly, in some embodiments, platelet counts can increase by at least about 25%, in other embodiments at least about 50%, and in further embodiments at least about 100%. A person of ordinary skill in the art will recognize that additional ranges of blood parameter improvement within the explicit ranges presented are contemplated and are within the present disclosure.

The activation compounds, such as one or more cytokines and/or one or more ionophore, can be mixed with an appropriate cell culture medium or a portion thereof for distribution. In alternative embodiments, one or more activation compounds can be packaged along with a cell culture medium or portions thereof for shipping. Similarly, a desired combination of activation compounds, such as one or more cytokines and one or more ionopores, can be packaged together for shipping, either mixed or in separate compartments. In any of these embodiments, the medium and/or activation compounds can be combined with any remaining medium components and/or activation compounds to form the desired medium for culturing cells under conditions to activate the cells. Also, in any of these embodiments, the compositions that are packaged together can include, for example, instructions for completing the cell culture medium with activation properties and/or instructions for performing the cell culturing.

The cell culturing can be performed at the facility that is treating the patient or the cell culturing to activate the cells can be performed at a remote location. In either case, the activated cells can be administered after a short period of time after harvesting from the cell culture to ensure that the cells remain viable. Alternatively, the cells can be stored under conditions that maintain the cells in a viable condition. For example, the cells can be stored at liquid nitrogen temperatures with a cryoprotectant. The cells can be prepared, for example using known procedures, at appropriate times for administration to the patient. For example, the cells can be suspended in a buffered saline solution for administration to the patient. Other known carriers, for example, can be used for delivery of the cells.

EXAMPLES

Example 1—Treatment of Aplastic Anemia

I. Patients

Eight patients with verified histories of from one to six years of occupational exposure to benzene were subjected to the present regimen after their consents were obtained. The makeup of the patients was one male and seven females and the ages of the patients ranged from 24 to 41. All patients experienced symptoms of weakness, dizziness, fainting, and accelerated heart rates. Among these patients, four were hospitalized due to acute symptoms with bleeding. The hospitalized patients required blood or platelet transfusions. The other four patients experienced chronic symptoms and were treated with standard therapies for four, six and 15 months, respectively. Bone marrow biopsies and aspiration samples were obtained from all patients to confirm hematopoiesis. Toxic levels of benzene were present in the blood and bone marrow of all patients.

II. Purification of Peripheral Blood Mononuclear Cells and Cell Culture

Peripheral blood mononuclear cells (PBMCs) were separated from patient blood samples (40–50 ml) by Ficoll-Hypaque centrifugation. The separated PBMCs were then placed in an appropriate volume (based on cell concentration) of RPMI 1640 with 10% fetal bovine serum under sterile conditions and cultured at $2\times10^6$ cells/ml for 48 hours in the presence of interleukin-2 (IL-2) at 500 IU/ml (Chiron, Emeryville, Calif.), granulocyte macrophage-colony-stimulating factor (GM-CSF) at 200 IU/ml (Immunex, Seattle, Wash.), and calcium ionophore A23187 at 100 ng/ml (Sigma, St. Louis, Mo.). At the end of the culture period, adherent cells were scraped off the plastic surfaces of the culture vessels and harvested together with non-adherent cells. To harvest the cells, the cells were spun down to form a cell pellet. Different numbers of cells were obtained for different patients. The harvested cells were washed twice in saline solution and administered to the patients. After washing, the cells were resuspended in 5 to 10 mls of saline, with the volume determined by the number of cells. These suspensions were farther diluted with 50 ml of saline before administering the cells to the patients.

Treatment Protocol

Activated allogeneic PBMCs were used for a single patient (HC) in the first three treatments because the patient had experienced low blood counts, severe bleeding and infection. For the other patients, activated PBMCs were intravenously administered with 50 ml saline to the patients. The treatment was repeated every week for at least four weeks. The number of cells administered to a particular patient depended on the number of cells obtained from the patient.

III. Results

Hematological Parameters

Hematological parameters, white blood cell counts, red blood cell counts, hemoglobin levels, and platelet counts, were monitored before and after the treatment for each patient and are shown in Table 1. Data from these patients indicated that the therapy was effective in enhancing the peripheral blood cell counts. Six patients experienced improvement of more than one subset listed and two patients had better platelet counts. The blood cell counts began to improve in most patients after two treatments and continued to improve throughout the time the present activated cells were administered. Seven of the eight patients improved to the extent that some of their hemological parameters reach normal levels or levels approaching normal after completion of four treatments. Although blood cell counts of the patients improved from the therapy in general, improvements were not uniformly achieved. Some patients experienced limited improvement in red blood cell counts, but dramatic improvement in platelet counts. It was noted that all patients' platelet counts were significantly increased.

Patient HC experienced more severe acute symptoms than the other patients. Additionally, patient HC had a bleeding problem as well. Because of the low yields of peripheral blood cells from patient HC, allogeneic PBMCs were used to stimulate patient HC's hematopoiesis. After three treatments using allogeneic cells, patient HC's blood counts began to improve. After the three treatments of allogeneic cells, autologous PBMCs were then used to continue the therapy. Although patient HC's hemotological parameters were not corrected to normal levels after six treatments, patient HC continued to improve.

Discomfort due administering the present immunotherapy was mild to moderate. Five patients experienced no appreciable discomfort. Three patients experienced chilling, fevers between 37 and 39 degrees C., headaches, nausea, vomiting, and loss of appetite after cell infusion. However, these symptoms were transient, typically lasting one to two days. Aspirin was administered when patients experienced discomfort.

Bone Marrow Hematopoiesis

Bone marrow biopsies and aspiration samples were obtained from all patients before the therapy began and two weeks after the final treatment. As shown in FIG. 1, the histology of the bone marrow samples from three patients with the most severe samples indicated severe damage before the therapy was begun. After the therapy was administered, remarkable improvements in bone marrow histology were found. With respect to patient HC, however, the improvement observed in patient HC's bone marrow was not coupled with improved peripheral blood counts.

Blood Transfusion

Before beginning treatment, four of the eight patients experienced severe symptoms, coupled with bleeding. These four patients required periodic transfusions of whole blood or platelets before and during the therapy. After four treatments, however, none of the patients experienced bleeding and whole blood and platelet transfusions were not continued.

Duration

Figure 2:
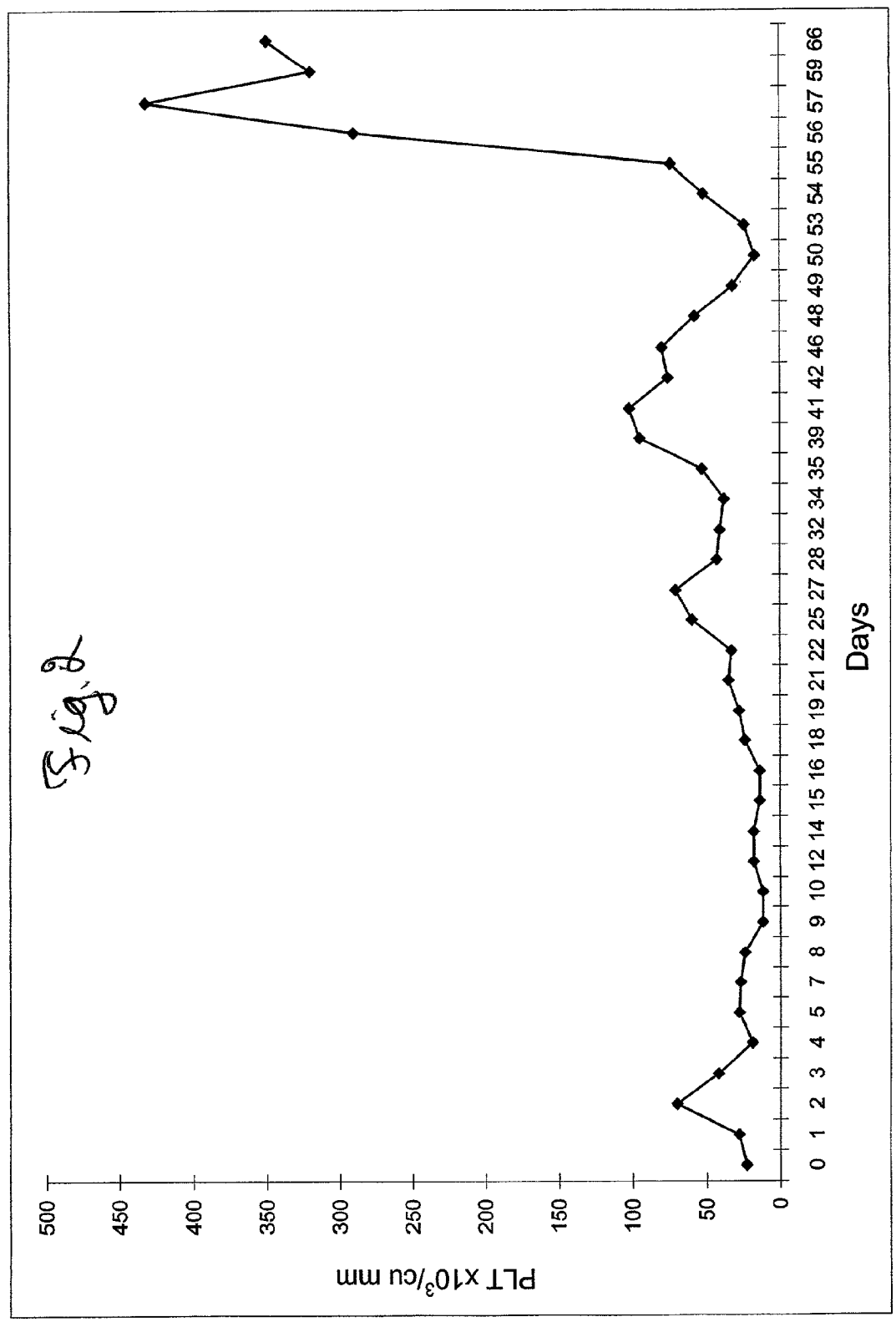
FIG. 2 is a plot of platelet count in platelets per cubic millimeter as a function of days after starting treatment with activated cells for a child pateint with platelet deficiency.

The beneficial effects of the present cell-based therapy do not appear to be transient. All patients continued to have improved or stable hematological parameters after the therapy was discontinued. Some female patients experienced unstable blood counts during menstrual periods, but no patients experienced a relapse. Patient LC, who responded to the therapy, has experienced stable symptoms for more than two months since the final treatment (FIG. 2).

Discussion

The results of this study suggest that administering activated PBMCs to patients with aplastic anemia is highly effective.

Some patients had close to normal bone marrow histologically, but had peripheral hematological parameters which were not as close to normal. To this end, it seemed that a time gap occurred between histological recovery of bone marrow and recovery of peripheral blood cell counts. Patients experiencing this gap were closely monitored and the patients' hematological parameters showed continued improvement. These patients sometimes took a few weeks or months to attain normal peripheral blood cell counts.

In analyzing the data generated by the study, it was noted that, among different compartments of the blood, increase in platelets was most evident, significant and rapid in patients benefiting from therapy. The initial increase in platelet counts was possibly due to the fact that platelets have a faster generation and differentiation interval. Other cell types of blood such as neutrophils, granulocytes and reticulocytes were also improved in agreement with the four parameters listed (data not shown). Platelet counts are likely more susceptible to benzene toxicity than other blood cells, but are the most responsive to the present therapy due to their faster generation interval.

Acquired aplastic anemia is a difficult disease to cure. However, the present immunosuppression therapy was very effective in treating this disease, for which bone marrow transplants are the only known cure heretofore. However, in spite of the success of bone marrow transplants, this therapy has serious complications, e.g., tumors, (Socie et al., Malignant tumors occurring after treatment of aplastic anemia, N. Eng. J. Med. 1993; 329(16): 1152–1157) and graft-versus-host disease (Ferrara et al., Graft-versus-host disease, N. Engl. J. Med. 1991(324); 324: 667–674). Moreover, many patients cannot obtain bone marrow transplants due to the expense of the procedure and/or the lack of compatible donors. To this end, a simple and effective therapy with fewer side effects is needed to treat aplastic anemia. The results of this study indicate that aplastic anemia can be effectively treated with minimal side effects. The present cell-based immunotherapy is believed to be applicable to other types of anemia and bone marrow disorders as well. These disorders include those experienced by HIV (human immunodeficiency virus)-infected patients after cocktail chemotherapy and cancer patients with bone marrow failure after chemotherapy and radiotherapy, inherited aplastic anemia, and idiopathic thrombocytopenic purpura.

While not wishing to be bound by a specific theoretical basis for the operation of this invention, it is presently believed that several phenomena may be responsible for the favorable responses of patients to the present immunotherapy. A first theory is that the activated cells secrete multiple (perhaps partially unknown) effective factors simultaneously. These multiple factors, when working in concert, may have a synergistic combined effect. A second factor hypothesized for the effectiveness of the present therapy is that some presently unknown key factors for hematopoiesis are produced by activated immune cells. These unknown factors may be responsible, at least in part, for the effectiveness of the present therapy. A third factor which might be involved is that immune cells are capable of traveling to bone marrow and of delivering cytokines to hematopoietic stem cells and to other precursor cells at close range. Moreover, the present activated immune cells may be able to remain in close proximity to the marrow for periods sufficient to effect microenvironment improvement in the bone marrow. A fourth factor which might be responsible for the effectiveness of the present therapy is that cell contact between immune cells and hematopoietic cells may be essential for hematopoietic cell growth and differentiation. A fifth factor might be that activated immune cells, even in small amounts, may contribute to prevent the immune system from adversely influencing hematopoiesis. Quantities of PCMBs from 10–100 ml of blood are relatively small. However, these small quantities exerted large effects on bone marrow histology and hematopoiesis.

The results of administering blood cells activated by the present protocol are unexpected in view of results from previous studies. With the exception of one study, Young et al. (note 2) found administered growth factors (granulocyte-colony stimulating factor and granulocyte macrophage-colony stimulating factor) to affect neutrophil numbers only. The one study showed marked increases of neutrophil and platelet counts when granulocyte-colony stimulating factor was administered. Interleukin-3, administered alone or in combination with granulocyte macrophage stimulating factor had even less effect on myelopoiesis than the growth factors administered alone. Similarly (Liu et al., Cellular interactions in hemopoiesis, Blood Cells 1987; 13: 101–110 and Ettinghausen et al., Hematologic effects if immunotherapy with lymphokine-activated killer cells and recombinant interleukin-2 in cancer patients, Blood 1987; 69(6): 1654–1660), found that administering activated pheipheral blood mononuclear cells and interleukin-2 to patients "emphasized" anemia and oesinophilia in patients receiving this therapy.

The present invention is also contemplated to include items of manufacture, which include separately packaged containers of one or more cytokine(s) and ionophore(s) as more fully described above. The container contents may be used to culture, and thereby activate, blood cells for use in the present therapeutic protocol. Instructions, such as on a label, may be present in the item of manufacture. A medium suitable for culturing blood cells may further be included.

Example 2—Treatment of Platelet Deficiency

This example described the treatment of a 1 year five month old female patient with idiopathic thrombocytopenic purpura. The patient was diagnosed with the disease at about 9 months.

The patient was first treated with conventional therapy of corticosteroids and intravenous infusiions of immunoglobulin. Although the patient esponded to the conventional treatment, the patient became completely dependent on the corticosteroid therapy. The maintain sufficient platelet levels, the patient had to receive increasingly higher doses of corticosteroids.

Then, the patient was treated with an activated cell based therapy as described herein. The treatment was the same as described in Example 1 except that only 20 mls of blood was drawn from the patient each time, rather than 40–50 mls. The patient was treated once a week for 9 weeks. Ex vivo activated cells were administered on day 1, day 8, day 15, day 22, day 29, day 35, day 42, day 49 and day 56. At the same time that immunotherapy with activated cells was initiated, corticosteroids and any other aspect of conventional therapy were completely withdrawn. The patient's platelet levels gradually improved during the treatment with activated cells as shown in FIG. 2. The patient had a lung infection at day 49 that correlated with a significant decrease in platelet number. After the patient recovered from the infection, the patient's platelet numbers went back to normal levels.

All publications, patents, patent applications, and other documents cited herein are hereby incorporated by reference in their entirety. In the case of conflict, the present specification shall prevail.

Because numerous modifications of this invention may be made without departing from the spirit thereof, the scope of the invention is not to be limited to the embodiments illustrated and described. Rather, the scope of the invention is to be determined by the appended claims and their equivalents.

What is claimed is:

1. A process of treating a patient with a deficiency in the number of red blood cells, white blood cells, or platelets, or in bone marrow hematopoiesis, comprising administering a therapeutically effective amount of ex vivo cultured activated peripheral blood mononuclear cells to the patient to increase concentrations of red blood cells, white blood cells, or platelets or to increase bone marrow hematopoiesis, wherein the ex vivo cultured activated cells are activated and cultured in the presence of a cytokine and a calcium ionophore wherein the cytokine is selected from the group consisting of regulatory protein Interleukin-2, granulocyte-macrophage colony stimulating factor and combinations thereof.

2. The process of claim 1, in which the calcium ionophore comprises A23187.

3. The process of claim 1, in which the cytokine comprises interleukin-2.

4. The process of claim 1, in which the cytokine comprises granylocyte-macrophage-colony stimulating factor.

5. The process of claim 1, in which the peripheral blood mononuclear cells are autologous to the patient.

6. The process of claim 1, in which the peripheral blood mononuclear cells are allogeneic to the patient.

7. The process of claim 1, in which the peripheral blood mononuclear cells are cultured in the presence of a mammalian serum.

8. The process of claim 1, in which the peripheral blood mononuclear cells are cultured in the presence of fetal bovine serum.

9. The process of claim 1, in which the peripheral blood mononuclear cells are from an immunologically acceptable donor.

10. The process of claim 1 in which the blood deficiency is selected from the group consisting of anemia, aplastic anemia and platelet deficiencies.

TABLE 1

Hematological Profiles of Patients Before and After Cell-Based Immune Therapy.

| Patients | Age/Sex | No. of Treament | Disease Type | WBC ($\times 10^3$/mL) | RBC ($\times 10^6$/mL) | HGB (g/dl) |
|---|---|---|---|---|---|---|
| HC | 32/F | 6 | Acute | 2.7 +/−0.2 | 1.2 +/−0.1 | 4.0 +/− 0.3 |
| YM | 29/F | 4 | Chronic | 3.6 +/−0.3 | 3.8 +/−0.5 | 11.1 +/− 0.4 |
| TB | 33/F | 4 | Acute | 3.2 +/−0.2 | 2.3 +/−0.3 | 8.4 +/− 0.4 |
| LC | 25/M | 4 | Acute | 1.4 +/−0.2 | 1.6 +/−0.3 | 5.7 +/− 0.3 |
| YX | 25/F | 4 | Chronic | 2.5 +/−0.3 | 2.7 +/−0.2 | 8.2 +/+ 0.4 |
| JX | 29/F | 5 | Acute | 2.7 +/−0.7 | 3.0 +/−0.2 | 8.1 +/− 3.4 |
| ZL | 41/F | 4 | Chronic | 3.1 +/−0.6 | 4.0 +/−0.6 | 12.6 +/− 1.9 |
| SC | 29/F | 4 | Chronic | 2.4 +/−0.3 | 2.6 +/−0.1 | 10.0 +/− 3.5 |

| Patients | PLT ($\times 10^3$/mm$^3$) | WBC ($\times 10^3$/mL) | RBC ($\times 10^6$/mL) | HGB (g/dl) | PLT ($\times 10^3$/mm$^3$) |
|---|---|---|---|---|---|
| HC | 28 +/− 3 | 3.8 +/− 0.25 | 2.0 +/− 0.2 | 7.0 +/− 0.3 | 43 +/− 3 |
| YM | 99 +/− 11 | 6.7 +/− 0.3 | 3.9 +/− 0.4 | 12.7 +/− 0.5 | 182 +/− 17 |
| TB | 47 +/− 5 | 4.7 +/− 0.3 | 3.2 +/− 0.3 | 11.5 +/− 0.7 | 107 +/− 11 |
| LC | 16 +/− 7 | 5.7 +/− 0.2 | 4.8 +/− 0.3 | 13.5 +/− 0.7 | 135 +/− 14 |
| YX | 22 +/− 3 | 3.5 +/− 0.3 | 2.8 +/− 0.2 | 9.8 +/− 0.5 | 100 +/− 10 |
| JX | 44 +/− 18 | 4.5 +/− 0.7 | 3.6 +/− 0.1 | 12.0 +/− 0.4 | 126 +/− 8 |
| ZL | 154 +/− 35 | 3.7 +/− 0.1 | 4.3 +/− 0.02 | 13.2 +/− 1.3 | 187 +/− 21 |
| SC | 54 +/− 4 | 2.8 +/− 0.2 | 2.9 +/− 0.2 | 11.0 +/− 0.3 | 71 +/− 8 |

The hematological parameters were measured and analyzed for five consecutive days before and after the therapy. Data are expressed as means +/− standard deviation. WBC indicates white blood cells; RBC indicates red blood cells; HGB indicates hemoglobin; PLT indicates platelets.

11. The process of claim 1 in which the blood deficiency is anemia.

12. The process of claim 1 in which the blood deficiency is aplastic anemia.

13. The process of claim 1 in which the blood deficiency is a platelet deficiency.

14. The process of claim 1 in which the administration is performed by intravenous injection.

15. The process of claim 1 in which the administering of the ex vivo cultured activated cells comprises the administration of multiple doses.

16. The process of claim 15 in which the multiple doses are administered over at least about 4 weeks.

17. The process of claim 15 which the cells are cultured in serum-less medium.

18. The process of claim 15 in which the multiple doses are administered over at least about 1 week.

19. The process of claim 1 in which the peripheral blood mononuclear cells are cultured in the presence of interleukin-2, granulocyte-macrophage colony stimulating factor and a calcium ionophore.

20. The process of claim 1 in which the patient is a cancer patient experiencing a deficiency in bone marrow hematopoiesis after chemotherapy.

21. The process of claim 1 in which the patient is a cancer patient experiencing a deficiency in bone marrow hematopoiesis after radiotherapy.

* * * * *